(12) United States Patent
Yamaguchi

(10) Patent No.: US 10,000,774 B2
(45) Date of Patent: Jun. 19, 2018

(54) TRANSFORMANT FOR EXPRESSING CIS-PRENYLTRANFERASE AND NOGO B RECEPTOR

(71) Applicant: SUMITOMO RUBBER INDUSTRIES, LTD., Kobe-shi, Hyogo (JP)

(72) Inventor: Haruhiko Yamaguchi, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 29 days.

(21) Appl. No.: 15/107,178

(22) PCT Filed: Jan. 6, 2015

(86) PCT No.: PCT/JP2015/050077
§ 371 (c)(1),
(2) Date: Jun. 22, 2016

(87) PCT Pub. No.: WO2015/107920
PCT Pub. Date: Jul. 23, 2015

(65) Prior Publication Data
US 2017/0009259 A1 Jan. 12, 2017

(30) Foreign Application Priority Data

Jan. 20, 2014 (JP) .................... 2014-007779

(51) Int. Cl.
| | | |
|---|---|---|
| *C12N 5/04* | (2006.01) | |
| *C12N 1/20* | (2006.01) | |
| *C12N 15/00* | (2006.01) | |
| *C12N 9/10* | (2006.01) | |
| *C12P 5/00* | (2006.01) | |
| *C07H 21/04* | (2006.01) | |
| *C07H 21/02* | (2006.01) | |
| *C07K 14/00* | (2006.01) | |
| *C12N 15/82* | (2006.01) | |
| *C07K 14/705* | (2006.01) | |
| *C07K 14/415* | (2006.01) | |

(52) U.S. Cl.
CPC ............ *C12P 5/007* (2013.01); *C07K 14/415* (2013.01); *C07K 14/705* (2013.01); *C12N 9/1085* (2013.01); *C12N 15/8201* (2013.01); *C12Y 205/0102* (2013.01)

(58) Field of Classification Search
None
See application file for complete search history.

(56) References Cited

FOREIGN PATENT DOCUMENTS

JP 2005-500840 A 1/2005

OTHER PUBLICATIONS

Branden et al. Introduction to Protein Structure, Garland Publishing Inc., New York, p. 247, 1991.*
Surmacz. cis-Prenyltransferase AtCPT6 produces a family of very short-chain polyisoprenoids in planta. Biochimica et Biophysica Acta 1841 (2014) 240-250.*
Asawatreratanakul et al., "Molecular cloning, expression and characterization of cDNA encoding cis-prenyltransferases from Hevea brasiliensis. A key factor participating in natural rubber biosynthesis," Eur. J. Biochem., vol. 270, 2003, p. 4671-4680.
Dai et al., "In-depth proteome analysis of the rubber particle of *Hevea brasiliensis* (para rubber tree)," Plant Mol. Biol., vol. 82, 2013 (published online Apr. 4, 2013), p. 155-168.
Harrison et al., "Nogo-B receptor is necessary for cellular dolichol biosynthesis and protein N-glycosylation," The EMBO Journal, vol. 30, No. 12, 2011 (published online May 13, 2011), p. 2490-2500.
Hillebrand et al., "Down-Regulation of Small Rubber Particle Protein Expression Affects Integrity of Rubber Particles and Rubber Content in Taraxacum brevicorniculatum," PLoS ONE, Jul. 23, 2012, vol. 7, Issue 7, p. 1-9.
Park et al., "Mutation of Nogo-B receptor, a subunit of cis-prenyltransferase, causes a congenital disorder of glycosylation," Cell Metabolism, vol. 20, Sep. 2, 2014 (published Jul. 24, 2014), p. 448-457.
Post et al., "Laticifer-specific cis-prenyltransferase silencing affects the rubber, triterpene, and inulin content of Taraxacum brevicorniculatum," Plant Physiology, Mar. 2012 (published Jan. 11, 2012), vol. 158, p. 1406-1417.
Priya et al., "Differential expression pattern of rubber elongation factor (REF) mRNA transcripts from high and low yielding clones of rubber tree (*Hevea brasiliensis* Muell. Arg.)," Plant Cell Reports, 2007 (published online Jul. 14, 2007), vol. 26, pp. 1833-1838.
Qu et al., "A lettuce (*Lactuca sativa*) homolog of human Nogo-B receptor interacts with cis-prenyltransferase and is necessary for natural rubber biosynthesis," J. Biol. Chem., Jan. 23, 2015, 2 pages.
Rahman et al., "Draft genome sequence of the rubber tree *Hevea brasiliensis*," BMC Genomics, vol. 14, No. 75, 2013, p. 1-15.
Rahman et al., "TSA: Hevea brasiliensis contig33814, mRNA sequence," Database GenBank [online], Accession No. JT945746, Feb. 5, 2013, p. 1-2.
Takahashi et al., "Characterization of cis-prenyltransferases from the rubber producing plant *Hevea brasiliensis* heterologously expressed in yeast and plant cells," Plant Biotechnology, vol. 29, Oct. 20, 2012 (released Aug. 30, 2012), p. 411-417 (8 pages).
Epping et al., "A rubber transferase activator is necessary for natural rubber biosynthesis in dandelion," Nature Plants, vol. 1, May 2015, XP055372960, pp. 1-9.
Nature Chemical Biology, "Polymer Biosynthesis Rubber ramps up," vol. 11, Jul. 2015, XP055373184, 1 page.
Aoki et al., "Identification of laticifer-specific genes and their promoter regions from a natural rubber producing plant *Hevea brasiliensis*," Plant Science, vol. 225, 2014 (available online May 12, 2014), pp. 1-8.

(Continued)

*Primary Examiner* — Yong D Pak
(74) *Attorney, Agent, or Firm* — Birch, Stewart, Kolasch & Birch, LLP

(57) ABSTRACT

Provided are a transformant produced by introducing a gene coding for a cis-prenyltransferase and a gene coding for a Nogo-B receptor, which are considered to be involved in polyisoprenoid biosynthesis, into a host to allow the host to express the cis-prenyltransferase and the Nogo-B receptor, and a method for producing a polyisoprenoid using the transformant. The present invention relates to a transformant produced by introducing a gene coding for a cis-prenyltransferase and a gene coding for a Nogo-B receptor into a host to allow the host to express the cis-prenyltransferase and the Nogo-B receptor.

6 Claims, 1 Drawing Sheet

(56) References Cited

OTHER PUBLICATIONS

Berthelot et al., "Hevea brasiliensis REF (Hev b 1) and SRPP (Hev b 3): An overview on rubber particle proteins," Biochimie, vol. 106, 2014 (available online Jul. 11, 2014), pp. 1-9.
Hofmann, "The Who, What, and Where of Plant Polyprenol Biosynthesis Point to Thylakoid Membranes and Photosynthetic Performance," The Plant Cell, vol. 29, Jul. 2017, pp. 1552-1553.
Ohya et al., "Biosynthesis of natural rubber and other natural polyisoprenoids," Biopolymers Online, 2005 (Published online Jan. 15, 2005), 43 pages.
Rojruthai et al., "In vitro synthesis of high molecular weight rubber by Hevea small rubber particles," Journal of Bioscience and Bioengineering, vol. 109, No. 2, 2010 (available online Sep. 18, 2009), pp. 107-114.
Xiang et al., "Proteome analysis of the large and the small rubber particles of Hevea brasiliensis using 2D-DIGE," Plant Physiology and Biochemistry, vol. 60, 2012 (available online Sep. 5, 2012), pp. 207-213.

\* cited by examiner (a)
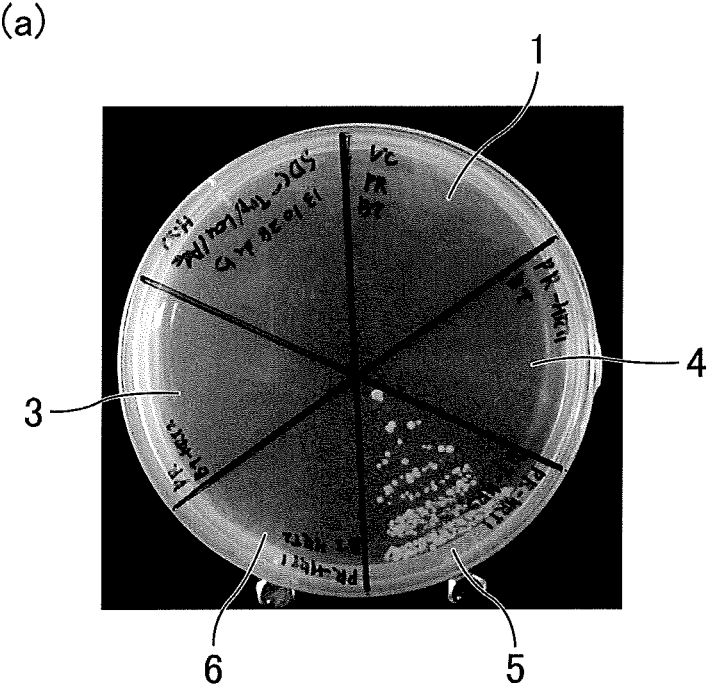
(b)
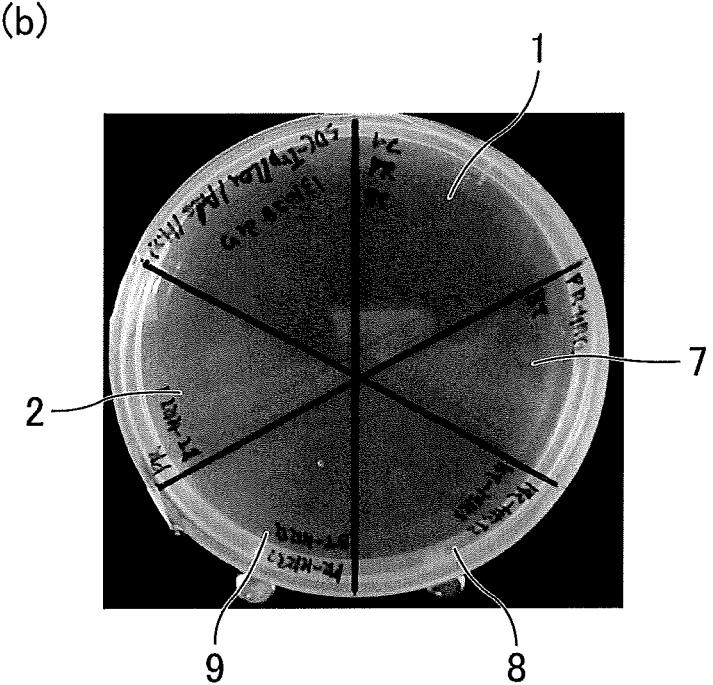

TRANSFORMANT FOR EXPRESSING CIS-PRENYLTRANFERASE AND NOGO B RECEPTOR

TECHNICAL FIELD

The present invention relates to a transformant produced by introducing a gene coding for a cis-prenyltransferase and a gene coding for a Nogo-B receptor into a host to allow the host to express the cis-prenyltransferase and the Nogo-B receptor, and a method for producing a polyisoprenoid using the transformant.

BACKGROUND ART

Nowadays natural rubber (one example of polyisoprenoids) for use in industrial rubber products are harvested from isoprenoid-producing plants, such as para rubber tree (*Hevea brasiliensis*) belonging to the family Euphorbiaceae, or Indian rubber tree (*Ficus elastica*) belonging to the family Moraceae.

At present, *Hevea brasiliensis* is virtually the only source for the natural rubber used in industrial rubber products. *Hevea brasiliensis* is a plant that can only be grown in certain regions, including Southeast Asia and South America. Moreover, *Hevea brasiliensis* trees take about seven years from planting to grow mature enough to yield rubber, and yields natural rubber only for a period of 20 to 30 years. Demand for natural rubber is expected to grow in the future, especially in developing countries, but for the reasons discussed above it is difficult to greatly increase natural rubber production from *Hevea brasiliensis*. There is therefore concern that natural rubber sources will dry up, and needs exist to develop stable natural rubber sources other than mature *Hevea brasiliensis* trees and to improve productivity of natural rubber from *Hevea brasiliensis*.

Natural rubber has a cis-1,4-polyisoprene structure, with isopentenyl diphosphate (IPP) unit, and the nature of this structure suggests that cis-prenyltransferase (CPT) is involved in natural rubber biosynthesis. For example, several CPTs are found in *Hevea brasiliensis*, including *Hevea* rubber transferase 1 (HRT1) and *Hevea* rubber transferase 2 (HRT2) (see, for example, Non Patent Literatures 1 and 2). It is also known that rubber synthesis can be reduced in the dandelion species *Taraxacum brevicorniculatum* by suppressing CPT expression (see, for example, Non Patent Literature 3).

Previous studies of proteins associated with natural rubber biosynthesis have focused on rubber elongation factor (REF) and small rubber particle protein (SRPP) (see, for example, Non Patent Literatures 4 and 5). However, the associations between these proteins and CPT are not completely understood.

It has also been suggested that Nogo-B receptor (NgBr) is involved in dolichol biosynthesis by a human CPT (see, for example, Non Patent Literature 6).

CITATION LIST

Non Patent Literature

Non Patent Literature 1: Rahaman et al., BMC Genomics, 2013, vol. 14
Non Patent Literature 2: Asawatreratanakul et al, European Journal of Biochemistry, 2003, vol. 270, pp. 4671-4680
Non Patent Literature 3: Post et al., Plant Physiology, 2012, vol. 158, pp. 1406-1417
Non Patent Literature 4: Hillebrand et al., PLoS ONE, 2012, vol. 7
Non Patent Literature 5: Priya et al., Plant Cell Reports, 2007, vol. 26, pp. 1833-1838
Non Patent Literature 6: K. D. Harrison et al., The EMBO Journal, 2011, vol. 30, pp. 2490-2500

SUMMARY OF INVENTION

Technical Problem

As discussed above, needs exist to develop stable natural rubber sources other than mature *Hevea brasiliensis* trees and to improve productivity of natural rubber from *Hevea brasiliensis*. At present, however, the biosynthesis mechanism of natural rubber, and particularly the regulatory mechanism remains largely unclear, and there is still much room for improvement to greatly increase natural rubber production. In this context, one possible approach to solving these problems is to stabilize and enhance the activity of CPT in natural rubber biosynthesis in order to increase natural rubber production.

In view of these circumstances, the present invention aims to provide a transformant produced by introducing a gene coding for a cis-prenyltransferase and a gene coding for a Nogo-B receptor, which are considered to be involved in polyisoprenoid biosynthesis, into a host to allow the host to express the cis-prenyltransferase and the Nogo-B receptor, and a method for producing a polyisoprenoid using the transformant.

Solution to Problem

The present invention relates to a transformant produced by introducing a gene coding for a cis-prenyltransferase and a gene coding for a Nogo-B receptor into a host to allow the host to express the cis-prenyltransferase and the Nogo-B receptor.

Preferably, at least one of the gene coding for a cis-prenyltransferase or the gene coding for a Nogo-B receptor is derived from a plant.

Preferably, at least one of the gene coding for a cis-prenyltransferase or the gene coding for a Nogo-B receptor is derived from an isoprenoid-producing plant.

Preferably, at least one of the gene coding for a cis-prenyltransferase or the gene coding for a Nogo-B receptor is derived from *Hevea brasiliensis*.

Preferably, the gene coding for a Nogo-B receptor is either of the following DNAs:

[3] a DNA having the nucleotide sequence of SEQ ID NO:5; and

[4] a DNA capable of hybridizing to a DNA having a nucleotide sequence complementary to the nucleotide sequence of SEQ ID NO:5 under stringent conditions.

Preferably, the gene coding for a cis-prenyltransferase is either of the following DNAs:

[1] a DNA having the nucleotide sequence of SEQ ID NO:1 or 3; and

[2] a DNA capable of hybridizing to a DNA having a nucleotide sequence complementary to the nucleotide sequence of SEQ ID NO:1 or 3 under stringent conditions, and coding for a protein having an enzyme activity that catalyzes a reaction of cis-chain elongation of an isoprenoid compound.

Preferably, the gene coding for a cis-prenyltransferase is either of the following DNAs:

[1-1] a DNA having the nucleotide sequence of SEQ ID NO: 1; and

[2-1] a DNA capable of hybridizing to a DNA having a nucleotide sequence complementary to the nucleotide sequence of SEQ ID NO:1 under stringent conditions, and coding for a protein having an enzyme activity that catalyzes a reaction of cis-chain elongation of an isoprenoid compound.

The host is preferably an isoprenoid-producing plant.

The present invention also relates to a method for producing a polyisoprenoid using the above-described transformant.

Advantageous Effects of Invention

The transformant of the present invention is produced by introducing a gene coding for a cis-prenyltransferase (CPT) and a gene coding for a Nogo-B receptor (NgBr) into a host to allow the host to express the CPT and NgBr. Since the CPT and NgBR are co-expressed in the host, the activity of CPT is expected to be stabilized and enhanced. Accordingly, it is expected that in the transformant, the amount of the products biosynthesized through the reactions catalyzed by CPT and therefore polyisoprenoid production is enhanced, and thus the use of such a transformant in polyisoprenoid production can result in increased polyisoprenoid yield.

BRIEF EXPLANATION OF DRAWINGS

FIG. 1 shows photographs illustrating the results of yeast two-hybrid analyses.

DESCRIPTION OF EMBODIMENTS

The inventor of the present invention made various studies for improving polyisoprenoid productivity. In the studies, they focused on cis-prenyltransferase (CPT) because it has been considered to be one of enzymes playing a key role in polyisoprenoid biosynthesis. According to a report (Non-Patent Literature 6), Nogo-B receptor (NgBr) interacts with CPT in humans to improve the stability of the CPT protein, thereby stabilizing and enhancing dolichol biosynthesis activity. This suggests the possible involvement of NgBr in the activity of CPT in organisms in general. In view of the above, the present inventor prepared a transformant engineered to express CPT and NgBr. In such a transformant, due to the coexistence of CPT and NgBr, the activity of CPT is expected to be stabilized and enhanced. Accordingly, it is expected that the amount of the products biosynthesized through the reactions catalyzed by CPT and therefore polyisoprenoid production is enhanced, resulting in increased polyisoprenoid yield.

The transformant of the present invention is produced by introducing a gene coding for a cis-prenyltransferase (CPT) and a gene coding for a Nogo-B receptor (NgBr) into a host to allow the host to express the CPT and NgBr.

The gene coding for a CPT and/or the gene coding for a NgBr may be of any origin, and is preferably derived from a plant, more preferably an isoprenoid-producing plant. The genes are still more preferably both derived from at least one isoprenoid-producing plant selected from the group consisting of *Hevea brasiliensis, Sonchus oleraceus, Parthenium argentatum*, and *Taraxacum kok-saghyz*, particularly preferably *Hevea brasiliensis*, among others.

(Amino Acid Sequence of cis-prenyltransferase (CPT))

The following protein [1] is a specific example of the CPT:

[1] a protein having the amino acid sequence of SEQ ID NO:2 or 4.

It is known that proteins having one or more amino acid substitutions, deletions, insertions, or additions relative to the original amino acid sequence can have the inherent function. Considering this fact, another specific example of the CPT is the following protein [2]:

[2] a protein having an amino acid sequence containing one or more amino acid substitutions, deletions, insertions and/or additions relative to the amino acid sequence of SEQ ID NO:2 or 4, and having the inherent function thereof.

The inherent function of the protein of SEQ ID NO:2 or 4 herein refers to the inherent function of CPT, that is, an enzyme activity that catalyzes a reaction of cis-chain elongation of an isoprenoid compound.

In order to maintain the enzyme activity, the amino acid sequence preferably contains one or more, more preferably 1-58, still more preferably 1-44, further more preferably 1-29, particularly preferably 1-15, most preferably 1-6, yet most preferably 1-3 amino acid substitutions, deletions, insertions and/or additions relative to the amino acid sequence of SEQ ID NO:2.

Also in order to maintain the enzyme activity, the amino acid sequence preferably contains one or more, more preferably 1-57, still more preferably 1-43, further more preferably 1-29, particularly preferably 1-15, most preferably 1-6, yet most preferably 1-3 amino acid substitutions, deletions, insertions and/or additions relative to the amino acid sequence of SEQ ID NO:4.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

It is also known that proteins with amino acid sequences having high sequence identity to the original amino acid sequence can also have similar function. Considering this fact, another specific example of the CPT is the following protein [3]:

[3] a protein having an amino acid sequence that has at least 80% sequence identity to the amino acid sequence of SEQ ID NO:2 or 4, and having the inherent function thereof.

In order to maintain the inherent function, i.e. the enzyme activity described above, the sequence identity to the amino acid sequence of SEQ ID NO:2 or 4 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether it is a protein having the above enzyme activity may be determined by conventional techniques, such as by expressing a target protein in a transformant prepared by introducing a gene coding for the target protein into *Escherichia coli* or other host organisms, and determining the presence or absence of the function of the target protein by the corresponding activity measurement method.

The CPT is preferably any of the following proteins:

[1-1] a protein having the amino acid sequence of SEQ ID NO:2;

[2-1] a protein having an amino acid sequence containing one or more amino acid substitutions, deletions, insertions, and/or additions relative to the amino acid sequence of SEQ ID NO:2, and having the inherent function thereof; and

[3-1] a protein having an amino acid sequence that has at least 90% sequence identity to the amino acid sequence of SEQ ID NO:2, and having the inherent function thereof.

The present inventor has found that, when the CPT is any of the above proteins, it interacts with NgBr. In this case, the activity of CPT is expected to be further stabilized and enhanced.

(Amino Acid Sequence of Nogo-B Receptor (NgBr))

The following protein [4] is a specific example of the NgBr:

[4] a protein having the amino acid sequence of SEQ ID NO:6.

As described above, it is known that proteins having one or more amino acid substitutions, deletions, insertions, or additions relative to the original amino acid sequence can have the inherent function. Thus, another specific example of the NgBr is the following protein [5]:

[5] a protein having an amino acid sequence containing one or more amino acid substitutions, deletions, insertions and/or additions relative to the amino acid sequence of SEQ ID NO:6, and having the inherent function thereof.

The inherent function of the protein of SEQ ID NO: 6 herein refers to the inherent function of NgBr, that is, the functions of binding to a membrane via one or more transmembrane domains on the N-terminal side of the protein, and interacting with another protein on the C-terminal side thereof. As a function of Nogo-B receptor in neurons, NgBr is known to interact with a myelin inhibitory protein (for example, Nogo-A) or the like, thereby being involved in signaling leading to neuronal growth-cone collapse and neurite outgrowth inhibition. Herein, however, the interaction involved in the above signaling is not included in the inherent function of the protein of SEQ ID NO: 6.

In order to maintain the inherent function, i.e. the function of NgBr, the amino acid sequence preferably contains one or more, more preferably 1 to 52, still more preferably 1 to 39, further more preferably 1 to 26, particularly preferably 1 to 13, most preferably 1 to 6, yet most preferably 1 to 3 amino acid substitutions, deletions, insertions, and/or additions relative to the amino acid sequence of SEQ ID NO:6.

Similarly to the above, among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

As described above, it is also known that proteins with amino acid sequences having high sequence identity to the original amino acid sequence can also have similar function. Thus, another specific example of the NgBr is the following protein [6]:

[6] a protein having an amino acid sequence that has at least 80% sequence identity to the amino acid sequence of SEQ ID NO: 6, and having the inherent function thereof.

In order to maintain the inherent function, i.e. the function of NgBr, the sequence identity to the amino acid sequence of SEQ ID NO:6 is preferably at least 85%, more preferably at least 90%, still more preferably at least 95%, particularly preferably at least 98%, most preferably at least 99%.

Whether it is a protein having a structure of NgBr may be determined by conventional techniques, such as by expressing a target protein in a transformant prepared by introducing a gene coding for the target protein into *Escherichia coli* or other host organisms, crushing the transformant followed by separation into fractions by centrifugation, and then observing strong expression in the membrane fraction by western blot analysis using a commercial anti-Nogo receptor antibody (e.g. Millipore, GeneTex).

(DNA Coding for cis-prenyltransferase (CPT))

The DNA coding for a CPT may be either of the following DNAs:

[1] a DNA having the nucleotide sequence of SEQ ID NO:1 or 3; and

[2] a DNA capable of hybridizing to a DNA having a nucleotide sequence complementary to the nucleotide sequence of SEQ ID NO:1 or 3 under stringent conditions, and coding for a protein having the inherent function thereof.

The inherent function of the protein encoded by the DNA having the nucleotide sequence of SEQ ID NO:1 or 3 herein is the same as the inherent function of the protein of SEQ ID NO:2 or 4.

As used herein, the term "hybridizing" means a process in which a DNA hybridizes to a DNA having a specific nucleotide sequence or a part of the DNA. Accordingly, the DNA having a specific nucleotide sequence or part of the DNA may have a nucleotide sequence long enough to be usable as a probe in northern or southern blot analysis or as an oligonucleotide primer in polymerase chain reaction (PCR) analysis. The DNA used as a probe may have a length of at least 100 bases, preferably at least 200 bases, more preferably at least 500 bases although it may be a DNA of at least 10 bases, preferably of at least 15 bases in length.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may have a nucleotide sequence that has at least 80%, preferably at least 90%, more preferably at least 95%, still more preferably at least 98%, particularly preferably at least 99% sequence identity to the nucleotide sequence of SEQ ID NO:1 or 3 as calculated using a program such as BLAST or FASTA with the parameters mentioned above.

Whether the DNA capable of hybridizing to the aforementioned DNA under stringent conditions codes for a protein having a predetermined enzyme activity may be determined by conventional techniques, such as by expressing a target protein in a transformant prepared by introducing a gene coding for the target protein into Escherichia coli or other host organisms, and determining the presence or absence of the function of the target protein by the corresponding activity measurement method.

The DNA coding for a CPT is preferably either of the following DNAs:

[1-1] a DNA having the nucleotide sequence of SEQ ID NO:1; and

[2-1] a DNA capable of hybridizing to a DNA having a nucleotide sequence complementary to the nucleotide sequence of SEQ ID NO:1 under stringent conditions, and coding for a protein having the inherent function thereof. The present inventor has found that, when the DNA coding for a CPT is either of the DNAs with above sequences, the expressed CPT interacts with NgBr. In this case, the activity of CPT is expected to be further stabilized and enhanced.

(DNA Coding for Nogo-B Receptor (NgBr))

The DNA coding for a NgBr may be either of the following DNAs:

[3] a DNA having the nucleotide sequence of SEQ ID NO:5; and

[4] a DNA capable of hybridizing to a DNA having a nucleotide sequence complementary to the nucleotide sequence of SEQ ID NO:5 under stringent conditions, and coding for a protein having the inherent function thereof.

Herein, the inherent function of the protein encoded by the DNA having the nucleotide sequence of SEQ ID NO:5 is the same as the inherent function of the protein of SEQ ID NO:6.

The term "hybridizing" herein is as described above. Also, the stringent conditions are as described above.

The DNA capable of hybridization under stringent conditions as described above may have a nucleotide sequence that has at least 80%, preferably at least 90%, more preferably at least 95%, still more preferably at least 98%, particularly preferably at least 99% sequence identity to the nucleotide sequence of SEQ ID NO:5 as calculated using a program such as BLAST or FASTA with the parameters mentioned above.

Whether the DNA capable of hybridizing to the aforementioned DNA under stringent conditions codes for a protein having a predetermined structure may be determined by conventional techniques, such as by expressing a target protein in a transformant prepared by introducing a gene coding for the target protein into Escherichia coli or other host organisms, crushing the transformant followed by separation into fractions by centrifugation, and then observing strong expression in the membrane fraction by western blot analysis using a commercial anti-Nogo receptor antibody (e.g. Millipore, GeneTex).

Conventional techniques may be employed to identify the amino acid sequence or the nucleotide sequence of the proteins. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the RACE method or the like is performed to identify the full-length nucleotide sequence or amino acid sequence. The RACE method (rapid amplification of cDNA ends method) refers to a method in which, when the nucleotide sequence of a cDNA is partially known, PCR is performed based on the nucleotide sequence information of such a known region to clone an unknown region extending to the cDNA terminal, and is capable of cloning the full-length cDNA by PCR without preparing a cDNA library.

The degenerate primers may each preferably be prepared from a plant-derived sequence having a highly similar sequence part to the target protein.

If the nucleotide sequence coding for the protein is known, it is possible to identify the full-length nucleotide sequence or amino acid sequence by designing a primer containing an initiation codon and a primer containing a termination codon using the known nucleotide sequence, followed by performing RT-PCR using a synthesized cDNA as a template.

(Transformant)

The gene coding for a CPT and the gene coding for a NgBr are introduced into a host to produce an organism (transformant) that has been transformed to express the CPT and the NgBr. Since the CPT and NgBr are co-expressed in the transformant, the activity of CPT is expected to be stabilized and enhanced. Accordingly, it is expected that in the transformant, the amount of the products biosynthesized through the reactions catalyzed by CPT and therefore polyisoprenoid production is enhanced, suitably resulting in increased polyisoprenoid yield.

The following briefly describes how to prepare the organism (transformant) transformed to express the CPT and NgBr. Such a transformant can be prepared by conventionally known methods.

Specifically, for example, the transformant may be prepared as follows: A DNA containing the nucleotide sequence of SEQ ID NO: 1 or 3, and a DNA containing the nucleotide sequence of SEQ ID NO:5 are inserted downstream of the promoter of a suitable expression vector with suitable restriction enzymes and the like to prepare a recombinant DNA. This recombinant DNA may then be introduced into host cells which are compatible with the expression vector, to obtain transformed cells. Alternatively, an expression vector in which a DNA containing the nucleotide sequence of SEQ ID NO:1 or 3 is inserted downstream of the promoter with suitable restriction enzymes and the like, and an expression vector in which a DNA containing the nucleotide sequence of SEQ ID NO:5 is inserted downstream of the promoter with suitable restriction enzymes and the like are used to prepare recombinant DNAs, and these recombinant DNAs may then be introduced into host cells which are compatible with the expression vectors, to obtain transformed cells.

Any host (host cells) capable of expressing the genes of interest may be used such as microorganisms, yeasts, animal cells, insect cells, plant cells, and other organisms, preferably eukaryotes. Since improved polyisoprenoid productivity and increased polyisoprenoid yield can be expected particularly when the CPT and NgBR are expressed in organisms capable of polyisoprenoid biosynthesis, the host is preferably a plant, more preferably an isoprenoid-producing plant, among others, and the host cells are preferably plant cells, more preferably cells of an isoprenoid-producing plant. Thus, in another suitable embodiment of the present invention, the host is an isoprenoid-producing plant.

The isoprenoid-producing plant is not particularly limited as long as it is capable of producing an isoprenoid. Examples include plants of the genus *Hevea*, such as *Hevea brasiliensis*; plants of the genus *Sonchus*, such as *Sonchus oleraceus, Sonchus asper*, and *Sonchus brachyotus*; plants of the genus *Solidago*, such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; plants of the genus *Helianthus*, such as *Helianthus annuus, Helianthus argophyllus, Helianthus atrorubens, Helianthus debilis, Helianthus decapetalus*, and *Helianthus giganteus*; plants of the genus *Taraxacum*, such as dandelion (*Taraxacum*), *Taraxacum venustum* H. Koidz, *Taraxacum hondoense* Nakai, *Taraxacum platycarpum* Dahlst, *Taraxacum japonicum, Taraxacum officinale* Weber, and *Taraxacum kok-saghyz*; plants of the genus *Ficus*, such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum, Parthenium hysterophorus*, and *Ambrosia artemisiifolia* (*Parthenium hysterophorus*); lettuce (*Lactuca sativa*) (*Lactuca serriola*), and *Ficus benghalensis*. The isoprenoid-producing plant is preferably at least one selected from the group consisting of plants of the genera *Hevea, Sonchus, Taraxacum*, and *Parhenium*, more preferably at least one selected from the group consisting of *Hevea brasiliensis, Sonchus oleraceus, Parthenium argentatum*, and *Taraxacum kok-saghyz*, among others.

The expression vector may be a vector that is capable of autonomous replication in the host cells or of being incorporated into the chromosome thereof, and contains a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in plant cells can be used. Examples include cauliflower mosaic virus (CaMV) 35S promoter, rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. Plant growth retardation and other adverse effects can be reduced by expressing specifically in a tissue in which an isoprenoid is biosynthesized.

The recombinant vector can be introduced by any method that allows the DNA to be introduced into host cells. Examples include methods using Agrobacterium (JP S59-140885 A, JP S60-70080 A, WO94/00977), electroporation (JP S60-251887 A), and methods using particle guns (gene guns) (JP 2606856 B, JP 2517813 B).

The transformant (transgenic plant cells) can be prepared by the above or other methods.

The present invention also provides an isoprenoid-producing plant into which have been introduced a gene coding for a CPT and a gene coding for a NgBr. The isoprenoid-producing plant is not particularly limited, as long as it is an isoprenoid-producing plant containing the transgenic plant cells. The isoprenoid-producing plant conceptually includes not only transgenic plant cells prepared by the above-described methods, but also, for example, all of their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or other techniques. Further, the transgenic plant cells, or their progeny or clones may be used to obtain reproductive materials (e.g. seeds, fruits, cuttings, stem tubers, root tubers, shoots, adventitious buds, adventitious embryos, calluses, protoplasts), which can then be used to produce the isoprenoid-producing plant on a large scale.

Techniques to regenerate plants from transgenic plant cells are already known; for example, Doi et al. disclose techniques for eucalyptus (JP H11-127025 A), Fujimura et al. disclose techniques for rice (Fujimura et al., (1995), Plant Tissue Culture Lett., vol. 2: p. 74-), Shillito et al. disclose techniques for corn (Shillito et al., (1989), Bio/Technology, vol. 7: p. 581-), Visser et al. disclose techniques for potato (Visser et al., (1989), Theor. Appl. Genet., vol. 78: p. 589-), and Akama et al. disclose techniques for *Arabidopsis thaliana* (Akama et al., (1992), Plant Cell Rep., vol. 12: p. 7-). Those skilled in the art can regenerate plants from the transgenic plant cells according to these documents.

Whether a target protein gene is expressed in a regenerated plant may be determined by well-known methods. For example, western blot analysis may be used to assess the expression of a target protein.

Seeds can be obtained from the transgenic plant, for example, as follows: the transgenic plant is rooted in an appropriate medium, transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the present invention, it is expected that the isoprenoid-producing plant into which have been introduced a gene coding for a CPT and a gene coding for a NgBr can be used in polyisoprenoid production to improve polyisoprenoid productivity. Specifically, polyisoprenoid production may be carried out by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. The transformant of the present invention is expected to have stabilized and enhanced CPT activity due to the proteins introduced therein. Accordingly, it is expected that the amount of the products biosynthesized through the reactions catalyzed by CPT and therefore polyisoprenoid production is enhanced, resulting in increased polyisoprenoid yield.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and naturalrubber. Theterm"isoprenoid" as used herein refers to a compound having isoprene ($C_5H_8$) units, and conceptually includes polyisoprenoids.

As described above, since the CPT and NgBr are co-expressed in the present invention, the activity of CPT is expected to be stabilized and enhanced. Accordingly, it is expected that the amount of the products biosynthesized through the reactions catalyzed by CPT and therefore polyisoprenoid production is enhanced in the transformant, resulting in increased polyisoprenoid yield. Thus, another aspect of the present invention relates to a method for producing a polyisoprenoid using a transformant produced by introducing a gene coding for a CPT and a gene coding for a NgBr into a host to allow the host to express the CPT and the NgBr.

Possible methods for increasing polyisoprenoid yield in the presence of both CPT and NgBr include, in addition to the method of using a transformant engineered to express both CPT and NgBr in vivo as described above, a method involving the presence of both CPT and NgBr in vitro, for example, by extracting crude enzymes from cells, purifying the CPT and NgBr, and allowing them to be present together in a test tube.

In the method involving the presence of both CPT and NgBr in vitro, the CPT and NgBr may be produced, for example, by inserting a gene coding for the CPT and/or a gene coding for the NgBr into an appropriate vector, and using transformed *Escherichia coli*, yeasts, or plants, cell-free protein expression systems, or other means.

The origin of the CPT used in the method involving the presence of both CPT and NgBr in vitro is not particularly limited, and the CPT is preferably derived from a eukaryote, more preferably a plant, still more preferably an isoprenoid-producing plant. The CPT may also be modified by any method, such as by adding a modification group to the enzyme (e.g. phosphorylation, methylation, acetylation, palmitoylation, myristoylation, farnesylation, sugar chain addition, or ubiquitination), or by oxidation/reduction of the disulfide group, or by structural modification with protease.

The origin of the NgBr used in the method involving the presence of both CPT and NgBr in vitro is not particularly limited, and the NgBr is preferably derived from a eukaryote, more preferably a plant, still more preferably an isoprenoid-producing plant. The NgBr may also be modified by any method, such as by adding a modification group to the enzyme (e.g. phosphorylation, methylation, acetylation, palmitoylation, myristoylation, farnesylation, sugar chain addition, or ubiquitination), or by oxidation/reduction of the disulfide group, or by structural modification with protease.

As described above, the present inventor has found that the CPT encoded by the DNA having the nucleotide sequence of SEQ ID NO:1 or the DNA capable of hybridizing to a DNA having a nucleotide sequence complementary to the nucleotide sequence of SEQ ID NO:1 under stringent conditions, and coding for a protein having the inherent function thereof, interacts with NgBr. Further to the CPT, NgBr is also considered to interact with a third protein. Examples of the mode of such interaction include the following two modes:

(1) The CPT interacts with the third protein via NgBr, or in other words, NgBr, the CPT, and the third protein simultaneously interact with one another.

(2) The interaction between NgBr and the CPT and the interaction between NgBr and the third protein occur individually.

Non-limiting examples of the third protein include rubber elongation factor (REF), small rubber particle protein (SRPP), and farnesyl diphosphate (FPP) synthase.

In the method involving the presence of both CPT and NgBr in vitro, in addition to the CPT and NgBr, another enzyme may further be added so as to be present together. Examples of the enzyme include enzymes known to be present in latex, such as rubber elongation factor (REF), small rubber particle protein (SRPP), small GTP-binding protein, hevein, β-1,3-glucanase, farnesyl diphosphate (FPP) synthase, and protease inhibitor proteins. Among these, enzymes interacting with NgBr, such as REF, are especially preferred.

In the method involving the presence of both CPT and NgBr in vitro, further components that may be added so as to be present together in addition to the CPT and NgBr are not limited to enzymes and may include membranes that serve to incorporate reaction products. The type of membrane is not particularly limited, and may be a natural membrane such as a cell membrane or small rubber particle, or an artificial membrane such as liposome.

The lipid forming the membrane may be a lipid that can form a lipid bilayer membrane, and examples include known glyceroglycolipids, sphingoglycolipids, cholesterol, and phospholipids.

Examples of the glyceroglycolipids include sulfoxyribosylglycerides, diglycosyldiglycerides, digalactosyldiglycerides, galactosyldiglycerides, and glycosyldiglycerides. Examples of the sphingoglycolipids include galactosylcerebrosides, lactosylcerebrosides, and gangliosides.

Examples of the phospholipids include natural or synthetic phospholipids, such as phosphatidylcholines, phosphatidylethanolamines, phosphatidylserines, phosphatidic acids, phosphatidylglycerols, phosphatidylinositols, lysophosphatidylcholines, sphingomyelins, egg yolk lecithin, soybean lecithin, and hydrogenated phospholipids.

Examples of the phosphatidylcholines include soybean phosphatidylcholine, egg yolk phosphatidylcholine, dilauroylphosphatidylcholine, dimyristoylphosphatidylcholine, dipalmitoylphosphatidylcholine, dioleoylphosphatidylcholine, and distearoylphosphatidylcholine.

Examples of the phosphatidylethanolamines include dioleoylphosphatidylethanolamine, dilauroylphosphatidylethanolamine, dimyristoylphosphatidylethanolamine, dipalmitoylphosphatidylethanolamine, and distearoylphosphatidylethanolamine.

Examples of the phosphatidylserines include dilauroylphosphatidylserine, dimyristoylphosphatidylserine, dipalmitoylphosphatidylserine, and distearoylphosphatidylserine.

Examples of the phosphatidylglycerols include dilauroylphosphatidylglycerol, dimyristoylphosphatidylglycerol, dipalmitoylphosphatidylglycerol, and distearoylphosphatidylglycerol.

Examples of the phosphatidylinositols include dilauroylphosphatidylinositol, dimyristoylphosphatidylinositol, dipalmitoylphosphatidylinositol, and distearoylphosphatidylinositol.

EXAMPLES

The present invention is specifically explained with reference to examples, but the present invention is not limited to these examples.

[Cloning]
(Identification of Amino Acid Sequence and Nucleotide Sequence of Target Protein)

Total RNA was extracted from *Hevea brasiliensis* latex by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for 5 minutes at 65° C., agitated using a vortex mixer, and centrifuged for 10 minutes at room temperature at 7000 rpm. After the centrifugation, the supernatant was transferred to a new tube, 12 mL of a phenol:chloroform (1:1) solution was added, and the mixture was agitated by shaking for 2 minutes. After the agitation, the resulting mixture was centrifuged again for 10 minutes at room temperature at 7000 rpm, the supernatant was transferred to a new tube, 12 mL of a chloroform:isoamyl alcohol (24:1) solution was added, and the mixture was agitated by shaking for 2 minutes. After the agitation, the resulting mixture was centrifuged again for 10 minutes at room temperature at 7000 rpm, the supernatant was transferred to a new tube, 1.2 mL of a 3M sodium acetate solution and 13 mL of isopropanol were added, and the mixture was agitated using a vortex mixer. The resulting mixture was incubated for 30 minutes at −20° C. to precipitate total RNA. The incubated mixture was centrifuged for 10 minutes at 4° C. at 15000 rpm, and the supernatant was removed to collect a precipitate of total RNA. The collected total RNA was washed twice with 70% ethanol, and then dissolved in RNase-free water.

cDNA was synthesized from the collected total RNA. The cDNA synthesis was carried out using a PrimeScript II 1st strand cDNA synthesis kit (Takara) in accordance with the manual.

CPT and NgBr genes were obtained using the prepared 1st strand cDNA as a template. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers:

```
Primer 1:
                                        (SEQ ID NO: 7)
5'-tttggccattacggccatggaattatacaacggtgagagg-3', Primer 2:
                                        (SEQ ID NO: 8)
5'-tttggccgaggcggccttattttaagtattccttatgtttc-3'.

The NgBr gene was obtained using the
following primers:
Primer 3:
                                        (SEQ ID NO: 9)
5'-tttggccattacggccatggatttgaaacctggag-3', Primer 4:
                                        (SEQ ID NO: 10)
5'-tttggccgaggcggcctcatgtaccataattttgctgcac-3'.
```

Two types of CPT genes (HRT1 and HRT2) and one type of NgBr gene (NgBr) were obtained as above. The three types of genes were sequenced to identify the full-length nucleotide sequence and amino acid sequence. The nucleotide sequence of HRT1 is given by SEQ ID NO:1, the nucleotide sequence of HRT2 is given by SEQ ID NO:3, and the nucleotide sequence of NgBr is given by SEQ ID NO:5. The amino acid sequence of HRT1 is given by SEQ ID NO:2, the amino acid sequence of HRT2 is given by SEQ ID NO:4, and the amino acid sequence of NgBr is given by SEQ ID NO:6.

(Vector Construction)

The resulting amplified three types of DNA fragments were subjected to dA addition and then inserted into pGEM-T Easy vectors using a pGEM-T Easy Vector System (Promega) to prepare pGEM-HRT1, pGEM-HRT2, and pGEM-NgBr.

(Transformation of E. coli)

Escherichia coli DH5α was transformed with the prepared vectors, the transformant was cultured on LB agar medium containing ampicillin and X-gal, and E. coli cells carrying the introduced target genes were selected by blue/white screening.

The E. coli cells transformed with the plasmids with the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

It was confirmed by sequence analysis that there were no mutations in the nucleotide sequences of the genes inserted into the collected plasmids

[Preparation of Yeast Transformed to Express Gene Coding for CPT and Gene Coding for NgBr]

HRT1, HRT2, and NgBr genes to be inserted into yeast expression vectors were obtained by PCR using the vectors prepared in the above "Vector construction" as templates.

The HRT1 and HRT2 genes were obtained using the following primers:

```
Primer 5:
                                        (SEQ ID NO: 11)
5'-gacgcccgggaggccatgaa-3', Primer 6:
                                        (SEQ ID NO: 12)
5'-cagcttcctcccgggctttg-3'.

The NgBr gene was obtained using the
following primers:
Primer 7:
                                        (SEQ ID NO: 13)
5'-tttctcgagatggatttgaaacctggagctg-3', Primer 8:
                                        (SEQ ID NO: 14)
5'-tttctcgagtgtaccataattttgctgcac-3'.
```

The obtained DNA fragments were subjected to dA addition and then inserted into pGEM-T Easy vectors using a pGEM-T Easy Vector System (Promega) to prepare pGEM-HRT1 YE, pGEM-HRT2 YE, and pGEM-NgBr YE.

Transformation of E. coli, collection of plasmids, and nucleotide sequence confirmation were performed as described in the above "Transformation of E. coli" but using the prepared vectors. The pGEM-HRT1 YE and pGEM-HRT2 YE, which were confirmed to have no mutations in the nucleotide sequence, were treated with the restriction enzyme SmaI and inserted into pGK426 treated similarly with SmaI, to prepare pGK-HRT1 and pGK-HRT2.

Similarly, the pGEM-NgBr YE, which was confirmed to have no mutations in the nucleotide sequence, was treated with the restriction enzyme XbaI and inserted into pGK425 treated similarly with XbaI, to prepare pGK-NgBr.

The yeast strain SNH23-7D was transformed with the prepared plasmids. The PEG method was used for the double transformation of the yeast. The transformant cells were cultured at 23° C. for three days on Leu- and Ura-deficient SD medium for screening. The pairs used in the preparation of double transformants of the yeast are as follows.

(1) SNH23-7D/pGK426, pGK425 (with no genes introduced)
(2) SNH23-7D/pGK-HRT1, pGK425 (HRT1 alone expressing strain)
(3) SNH23-7D/pGK-HRT2, pGK425 (HRT2 alone expressing strain)
(4) SNH23-7D/pGK-HRT1, pGK-NgBr (HRT1/NgBr co-expressing strain)
(5) SNH23-7D/pGK-HRT2, pGK-NgBr (HRT2/NgBr co-expressing strain)

No SNH23-7D/pGK426, pGK-NgBr transformant (NgBr alone expressing strain) was obtained.

[Yeast Two-Hybrid Screening]

The target genes inserted in the plasmids collected in the above "Cloning" were cleaved, by treatment with the restriction enzyme SfiI in order to insert the target genes into plasmids for yeast two-hybrid screening.

(Vector Construction)

The cleaved genes were inserted into yeast two-hybrid plasmids using Ligation high ver. 2 (Toyobo). The yeast two-hybrid bait plasmid used was pBT3-SUC bait vector, and the yeast two-hybrid prey plasmid used was pPR3-N prey vector. HRT1 or HRT2 was inserted into the prey vector (pPR-HRT1, pPR-HRT2), and HRT1, HRT2, or NgBr was inserted into the bait vector (pBT-HRT1, pBT-HRT2, pBT-NgBr).

(Transformation of *E. coli*)

*Escherichia coli* DH5a was transformed with the yeast two-hybrid vectors prepared as above. The transformant cells were cultured on LB agar medium containing ampicillin, and *E. coli* cells carrying the introduce target genes were selected.

The *E. coli* cells transformed with the plasmids with the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

(Yeast Double Transformation)

The yeast strain NMY-51 was transformed with the collected plasmids. The PEG method was used for the double transformation of the yeast. The transformant cells were cultured at 30° C. for three days on Trp- and Leu-deficient SD medium for screening. Table 1 shows the pairs used in the preparation of double transformants of the yeast.

TABLE 1

| No. | Prey | Bait |
|---|---|---|
| 1 | pPR3N | pBT3-SUC |
| 2 | pPR3N | pBT-HRT1 |
| 3 | pPR3N | pBT-HRT2 |
| 4 | pPR-HRT1 | pBT3-SUC |
| 5 | pPR-HRT1 | pBT-NgBr |
| 6 | pPR-HRT1 | pBT-HRT2 |
| 7 | pPR-HRT2 | pBT3-SUC |
| 8 | pPR-HRT2 | pBT-HRT1 |
| 9 | pPR-HRT2 | pBT-NgBr |

The double transformants of the yeast were observed for the interactions between the enzymes through yeast two-hybrid screening by culturing on Trp-, Leu-, Ade- and His-deficient SD medium for three days at 30° C. In this experiment, the yeast can grow on the selective medium only when a protein encoded by the gene introduced in the bait plasmid interacts with a protein encoded by the gene introduced in the prey plasmid.

The results of yeast two-hybrid screening analyses are shown in FIG. 1. FIG. 1(*a*) shows the results demonstrating whether or not HRT1 interacted with HRT2 or NgBr. FIG. 1(*b*) shows the results demonstrating whether or not HRT2 interacted with HRT1 or NgBr. In FIG. 1(*a*), the sections clockwise from the upper right correspond to the results of the pairs Nos. 1, 4, 5, 6, and 3, respectively, in Table 1. In FIG. 1(*b*), the sections clockwise from the upper right correspond to the results of the pairs Nos. 1, 7, 8, 9, and 2, respectively, in Table 1.

As shown in FIG. 1, only the results of the pair No. 5 in Table 1, i.e. the pair of HRT1 and NgBr, in FIG. 1(*a*) exhibited interaction. This indicated that NgBr interacts with HRT1 which is one type of CPT present in latex but does not interact with HRT2. It is thus demonstrated that NgBr does not interact with all types of CPT but interacts with a specific CPT.

From these results it is considered that the activity of HRT1 can be further stabilized and enhanced when HRT1 is combined with NgBr.

REFERENCE SIGNS LIST

1: a pair of pPR3N prey plasmid and pBT3-SUC bait plasmid
2: a pair of pPR3N prey plasmid and pBT-HRT1 bait plasmid
3: a pair of pPR3N prey plasmid and pBT-HRT2 bait plasmid
4: a pair of pPR-HRT1 prey plasmid and pBT3-SUC bait plasmid
5: a pair of pPR-HRT1 prey plasmid and pBT-NgBr bait plasmid
6: a pair of pPR-HRT1 prey plasmid and pBT-HRT2 bait plasmid
7: a pair of pPR-HRT2 prey plasmid and pBT3-SUC bait plasmid
8: a pair of pPR-HRT2 prey plasmid and pBT-HRT1 bait plasmid
9: a pair of pPR-HRT2 prey plasmid and pBT-NgBr bait plasmid (Sequence Listing Free Text)

SEQ ID NO:1: nucleotide sequence of gene coding for HRT1 from *Hevea brasiliensis*
SEQ ID NO:2: amino acid sequence of HRT1 from *Hevea brasiliensis*
SEQ ID NO:3: nucleotide sequence of gene coding for HRT2 from *Hevea brasiliensis*
SEQ ID NO:4: amino acid sequence of HRT2 from *Hevea brasiliensis*
SEQ ID NO:5: nucleotide sequence of gene coding for NgBr from *Hevea brasiliensis*
SEQ ID NO: 6: amino acid sequence of NgBr from *Hevea brasiliensis*
SEQ ID NO:7: Primer 1
SEQ ID NO:8: Primer 2
SEQ ID NO:9: Primer 3
SEQ ID NO:10: Primer 4
SEQ ID NO:11: Primer 5
SEQ ID NO:12: Primer 6
SEQ ID NO:13: Primer 7
SEQ ID NO:14: Primer 8

The invention claimed is:

1. A transformant of a *Hevea* or *Taraxacum* cell, produced by introducing a gene coding for a cis-prenyltransferase and a gene coding for a Nogo-B receptor into a *Hevea* or *Taraxacum* cell for the cell to express the cis-prenyltransferase and the Nogo-B receptor, wherein the gene coding for a Nogo-B receptor is either of the following DNAs:

a DNA comprising the nucleotide sequence of SEQ ID NO: 5; and a DNA having at least 90% sequence identity with the nucleotide sequence of SEQ ID NO: 5, wherein the gene coding for a cis-prenyltransferase is either of the following DNAs:
a DNA comprising the nucleotide sequence of SEQ ID NO: 1 or 3; and
a DNA having at least 90% sequence identity with the nucleotide sequence of SEQ ID NO: 1 or 3.

2. The transformant according to claim 1, wherein at least one of the gene coding for a cis-prenyltransferase or the gene coding for a Nogo-B receptor is derived from a plant.

3. The transformant according to claim 2, wherein at least one of the gene coding for a cis-prenyltransferase or the gene coding for a Nogo-B receptor is derived from an isoprenoid-producing plant.

4. The transformant according to claim 3, wherein at least one of the gene coding for a cis-prenyltransferase or the gene coding for a Nogo-B receptor is derived from *Hevea brasiliensis*.

5. The transformant according to claim 1, wherein the gene coding for a cis-prenyltransferase is either of the following DNAs:
a DNA comprising the nucleotide sequence of SEQ ID NO: 1; and
a DNA having at least 90% sequence identity with the nucleotide sequence of SEQ ID NO: 1.

6. A method for producing a polyisoprenoid using the transformant according to claim 1.

* * * * *

SEQUENCE LISTING

<160> NUMBER OF SEQ ID NOS: 14

<210> SEQ ID NO 1
<211> LENGTH: 873
<212> TYPE: DNA

<213> ORGANISM: Hevea brasiliensis

<400> SEQUENCE: 1

```
atggaattat acaacggtga gaggccaagt gtgttcagac tttagggaa gtatatgaga      60
aaagggttat atagcatcct aacccagggt cccatcccta ctcatattgc cttcatattg    120
gatggaaaca ggaggtttgc taagaagcat aaactgccag aaggaggtgg tcataaggct    180
ggattttag ctcttctgaa cgtactaact tattgctatg agttaggagt gaaatatgcg     240
actatctatg cctttagcat cgataatttt cgaaggaaac ctcatgaggt tcagtacgta    300
atggatctaa tgctggagaa gattgaaggg atgatcatgg aagaaagtat catcaatgca    360
tatgatattt gcgtacgttt tgtgggtaac ctgaagcttt taagtgagcc agtcaagacc    420
gcagcagata agattatgag ggctactgcc aacaattcca aatgtgtgct tctcattgct    480
gtatgctata cttcaactga tgagatcgtg catgctgttg aagaatcctc tgaattgaac    540
tccaatgaag tttgtaacaa tcaagaattg gaggaggcaa atgcaactgg aagcggtact    600
gtgattcaaa ttgagaacat ggagtcgtat tctggaataa aacttgtaga ccttgagaaa    660
aacacctaca taaatcctta tcctgatgtt ctgattcgaa cttctgggga gacccgtctg    720
agcaactact tactttggca gactactaat tgcatactgt attctcctca tgcactgtgg    780
ccagagattg gtcttcgaca cgtggtgtgg gcagtaatta acttccaacg tcattattct    840
tacttggaga aacataagga atacttaaaa taa                                 873
```

<210> SEQ ID NO 2
<211> LENGTH: 290
<212> TYPE: PRT
<213> ORGANISM: Hevea brasiliensis

<400> SEQUENCE: 2

```
Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80

Thr Ile Tyr Ala Phe Ser Ile Asp Asn Phe Arg Arg Lys Pro His Glu
                85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Gly Thr Val Ile Gln Ile Glu Asn Met Glu
```

```
            195                 200                 205
Ser Tyr Ser Gly Ile Lys Leu Val Asp Leu Glu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
            260                 265                 270

Ile Asn Phe Gln Arg His Tyr Ser Tyr Leu Glu Lys His Lys Glu Tyr
            275                 280                 285

Leu Lys
    290

<210> SEQ ID NO 3
<211> LENGTH: 855
<212> TYPE: DNA
<213> ORGANISM: Hevea brasiliensis

<400> SEQUENCE: 3
atggaattat acaacggtga gaggccaagt gtgttcagac ttttagggaa gtatatgaga    60
aaagggttat atagcatcct aacccagggt cccatcccta ctcatattgc cttcatattg   120 gatgaaacg ggaggtttgc taagaagcat aaactgccag aaggaggtgg tcataaggct    180 ggattttag ctcttctgaa cgtactaact tattgctatg agttaggagt gaaatatgcg    240
actatctatg cctttagcat cgataatttt cgaaggaaac tcatgaggt tcagtacgta    300 atgaatctaa tgctggagaa gattgaaggg atgatcatgg aagaaagtat catcaatgca   360
tatgatattt gcgtgcgttt tgttggtaat ctgaagcttt tagatgagcc actcaagacc   420
gcagcagata agataatgag ggctactgcc aaaaattcca aatttgtgct tctccttgct   480
gtatgctaca cttcaactga tgagatcgtg catgctgttg aagaatcctc taaggataaa   540
ttgaaatccg atgaaatttg caacgatgga aacggagatt gtgtgattaa aattgaggag   600
atggagccat attctgaaat aaaacttgta gagcttgaga aaacactta cataaatcct   660 tatcctgatg tcttgattcg aacttctggg gagacccgtc tgagcaacta cctactttgg   720
cagactacta attgcatact gtattctcct catgcactgt ggccagagat tggtcttcga   780
cacgtggtgt gggcagtaat taactgccaa cgtcattatt cttacttgga gaaacataag   840
gaatacttaa aataa                                                    855

<210> SEQ ID NO 4
<211> LENGTH: 284
<212> TYPE: PRT
<213> ORGANISM: Hevea brasiliensis

<400> SEQUENCE: 4

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Gly Arg Phe Ala Lys
        35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
```

```
                65                  70                  75                  80
Thr Ile Tyr Ala Phe Ser Ile Asp Asn Phe Arg Arg Lys Pro His Glu
                    85                  90                  95

Val Gln Tyr Val Met Asn Leu Met Leu Glu Lys Ile Glu Gly Met Ile
                100                 105                 110

Met Glu Glu Ser Ile Ile Asn Ala Tyr Asp Ile Cys Val Arg Phe Val
                115                 120                 125

Gly Asn Leu Lys Leu Leu Asp Glu Pro Leu Lys Thr Ala Ala Asp Lys
                130                 135                 140

Ile Met Arg Ala Thr Ala Lys Asn Ser Lys Phe Val Leu Leu Leu Ala
145                 150                 155                 160

Val Cys Tyr Thr Ser Thr Asp Glu Ile Val His Ala Val Glu Glu Ser
                165                 170                 175

Ser Lys Asp Lys Leu Lys Ser Asp Glu Ile Cys Asn Asp Gly Asn Gly
                180                 185                 190

Asp Cys Val Ile Lys Ile Glu Glu Met Glu Pro Tyr Ser Glu Ile Lys
                195                 200                 205

Leu Val Glu Leu Glu Arg Asn Thr Tyr Ile Asn Pro Tyr Pro Asp Val
                210                 215                 220

Leu Ile Arg Thr Ser Gly Glu Thr Arg Leu Ser Asn Tyr Leu Leu Trp
225                 230                 235                 240

Gln Thr Thr Asn Cys Ile Leu Tyr Ser Pro His Ala Leu Trp Pro Glu
                245                 250                 255

Ile Gly Leu Arg His Val Val Trp Ala Val Ile Asn Cys Gln Arg His
                260                 265                 270

Tyr Ser Tyr Leu Glu Lys His Lys Glu Tyr Leu Lys
                275                 280

<210> SEQ ID NO 5
<211> LENGTH: 774
<212> TYPE: DNA
<213> ORGANISM: Hevea brasiliensis

<400> SEQUENCE: 5
atggatttga aacctggagc tggagggcag agagttaatc gattagtgga tccgattagt      60
tatcattttc ttcaatttct gtggcgtact ctacatcttc ttgtcagctt atggtacctt     120
caagttagta tggtccaaat gatcgaaggc tttctaatct ctagtggact tgtgaaacgc     180
tatggagccc tcgatattga caaggtccgg taccttgcca ttgtggtaga tagtgaagaa     240
gcttaccaaa tttctaaagt tattcagctt ttgaaatggg tggaagatat gggtgtgaaa     300
catttatgcc tctatgattc aaaaggagtt ctcaagacaa acaagaaaac catcatggag     360
agtttgaaca atgctatgcc atttgaggaa gcagttgaaa aagatgtttt actgaccag     420 aaacagatga ctgtggaatt tgcttccagc tccgatggaa aggaagcaat aaccagggca     480
gctaacgtac tctttatgaa gtatttgaag atgctaaaa ctggtgtagg aaaggaagaa     540
ccatgcttta cagaagatca aatggatgag cactaaaag ctataggtta caaagggccg     600
gaacctgact tgctattaat ttatggacct gttagatgcc atctaggttt ctcaccgtgg     660
agacttcgat atactgagat ggtgcatatg ggacccttga ggtacatgaa cctcggttca     720
ctaaaaaagg ccattcacag gttcacaaca gtgcagcaaa attatggtac atga           774

<210> SEQ ID NO 6
<211> LENGTH: 257
<212> TYPE: PRT
```

<213> ORGANISM: Hevea brasiliensis

<400> SEQUENCE: 6

```
Met Asp Leu Lys Pro Gly Ala Gly Gly Gln Arg Val Asn Arg Leu Val
1               5                   10                  15
Asp Pro Ile Ser Tyr His Phe Leu Gln Phe Leu Trp Arg Thr Leu His
            20                  25                  30
Leu Leu Val Ser Leu Trp Tyr Leu Gln Val Ser Met Val Gln Met Ile
        35                  40                  45
Glu Gly Phe Leu Ile Ser Ser Gly Leu Val Lys Arg Tyr Gly Ala Leu
    50                  55                  60
Asp Ile Asp Lys Val Arg Tyr Leu Ala Ile Val Val Asp Ser Glu Glu
65                  70                  75                  80
Ala Tyr Gln Ile Ser Lys Val Ile Gln Leu Leu Lys Trp Val Glu Asp
                85                  90                  95
Met Gly Val Lys His Leu Cys Leu Tyr Asp Ser Lys Gly Val Leu Lys
            100                 105                 110
Thr Asn Lys Lys Thr Ile Met Glu Ser Leu Asn Asn Ala Met Pro Phe
        115                 120                 125
Glu Glu Ala Val Glu Lys Asp Val Leu Leu Asp Gln Lys Gln Met Thr
    130                 135                 140
Val Glu Phe Ala Ser Ser Ser Asp Gly Lys Glu Ala Ile Thr Arg Ala
145                 150                 155                 160
Ala Asn Val Leu Phe Met Lys Tyr Leu Lys Tyr Ala Lys Thr Gly Val
                165                 170                 175
Gly Lys Glu Glu Pro Cys Phe Thr Glu Asp Gln Met Asp Glu Ala Leu
            180                 185                 190
Lys Ala Ile Gly Tyr Lys Gly Pro Glu Pro Asp Leu Leu Ile Tyr
        195                 200                 205
Gly Pro Val Arg Cys His Leu Gly Phe Ser Pro Trp Arg Leu Arg Tyr
    210                 215                 220
Thr Glu Met Val His Met Gly Pro Leu Arg Tyr Met Asn Leu Gly Ser
225                 230                 235                 240
Leu Lys Lys Ala Ile His Arg Phe Thr Thr Val Gln Gln Asn Tyr Gly
                245                 250                 255
Thr
```

<210> SEQ ID NO 7
<211> LENGTH: 40
<212> TYPE: DNA
<213> ORGANISM: Artificial Sequence
<220> FEATURE:
<223> OTHER INFORMATION: Sense primer for CPT

<400> SEQUENCE: 7
tttggccatt acggccatgg aattatacaa cggtgagagg        40

<210> SEQ ID NO 8
<211> LENGTH: 41
<212> TYPE: DNA
<213> ORGANISM: Artificial Sequence
<220> FEATURE:
<223> OTHER INFORMATION: Antisense primer for CPT

<400> SEQUENCE: 8
tttggccgag gcggccttat tttaagtatt ccttatgttt c      41

```
<210> SEQ ID NO 9
<211> LENGTH: 35
<212> TYPE: DNA
<213> ORGANISM: Artificial Sequence
<220> FEATURE:
<223> OTHER INFORMATION: Sense primer for NgBr

<400> SEQUENCE: 9
tttggccatt acggccatgg atttgaaacc tggag                                35

<210> SEQ ID NO 10
<211> LENGTH: 40
<212> TYPE: DNA
<213> ORGANISM: Artificial Sequence
<220> FEATURE:
<223> OTHER INFORMATION: Antisense primer for NgBr

<400> SEQUENCE: 10
tttggccgag gcggcctcat gtaccataat tttgctgcac                           40

<210> SEQ ID NO 11
<211> LENGTH: 20
<212> TYPE: DNA
<213> ORGANISM: Artificial Sequence
<220> FEATURE:
<223> OTHER INFORMATION: Sense primer for HRT1,HRT2

<400> SEQUENCE: 11
gacgcccggg aggccatgaa                                                 20

<210> SEQ ID NO 12
<211> LENGTH: 20
<212> TYPE: DNA
<213> ORGANISM: Artificial Sequence
<220> FEATURE:
<223> OTHER INFORMATION: Antisense primer for HRT1,HRT2

<400> SEQUENCE: 12
cagcttcctc ccgggctttg                                                 20

<210> SEQ ID NO 13
<211> LENGTH: 31
<212> TYPE: DNA
<213> ORGANISM: Artificial Sequence
<220> FEATURE:
<223> OTHER INFORMATION: Sense primer for NgBr

<400> SEQUENCE: 13
tttctcgaga tggatttgaa acctggagct g                                    31

<210> SEQ ID NO 14
<211> LENGTH: 30
<212> TYPE: DNA
<213> ORGANISM: Artificial Sequence
<220> FEATURE:
<223> OTHER INFORMATION: Antisense primer for NgBr

<400> SEQUENCE: 14
tttctcgagt gtaccataat tttgctgcac                                      30
```